United States Patent [19]

Becherer et al.

[11] Patent Number: 5,780,612
[45] Date of Patent: *Jul. 14, 1998

[54] OLIGONUCLEOTIDES SPECIFIC FOR CYTOKINE SIGNAL TRANSDUCER GP130 MRNA

[75] Inventors: Kathleen Ann Becherer; Nanibhushan Dattagupta, both of San Diego, Calif.; Yathi M. Naidu, Park Ridge, Ill.

[73] Assignee: Gen-Probe Incorporated, San Diego, Calif.

[*] Notice: The term of this patent shall not extend beyond the expiration date of Pat. No. 5,674,995.

[21] Appl. No.: 943,834

[22] Filed: Oct. 3, 1997

Related U.S. Application Data

[63] Continuation of Ser. No. 476,634, Jun. 7, 1995, Pat. No. 5,674,995.
[51] Int. Cl.$^6$ .......................... C12N 15/00; C07H 21/00; C12Q 1/68
[52] U.S. Cl. .......................... 536/24.5; 435/6; 435/172.1; 536/23.1; 536/24.3; 536/24.1
[58] Field of Search ..................... 536/23.1, 24.1, 536/24.3, 24.5; 435/6, 172.1; 514/44

[56] References Cited

U.S. PATENT DOCUMENTS 5,252,723  10/1993  Bhatt ........................... 536/25.3

FOREIGN PATENT DOCUMENTS

| | | |
|---|---|---|
| 0411946 | 2/1991 | European Pat. Off. . |
| 9207864 | 5/1992 | WIPO . |
| 9310151 | 5/1993 | WIPO . |
| 9425036 | 11/1994 | WIPO . |
| 9503406 | 2/1995 | WIPO . |
| 9503427 | 2/1995 | WIPO . |
| 9533059 | 12/1995 | WIPO . |
| 9609382 | 3/1996 | WIPO . |

OTHER PUBLICATIONS

Bangham, et al. Diffusion of univalent ions across the lamellae of swollen phospholipids. *J. Med. Biol.* 13:238–252 (1965).

Caruthers, et al. Chemical synthesis of deoxyoligonucleotides by the phosphoramidite method. *Methods in Enzymology* 154:287–313 Academic Press, Inc. (1987).

Girasole, et al. Estradiol inhibits interleukin–6 production by bone marrow–derived stromal cells and osteoblasts in vitro: a potential mechanism for the antiosteoporotic effect of estrogens. *The Journal of Clinical Investigation, Inc.* 89:883–891 (1992).

Grossman, et al. Interleukin 6 is expressed in high levels in psoriatic skin and stimulates proliferation of cultured human keratinocytes. *Proc. Natl. Acad. Sci.* 86:6367–6371. Medical Sciences U.S.A. (1989).

Hibi, et al. Molecular cloning and expression of an IL–6 signal transducer, gp130. *Cell* 63:1149–1157 Cell Press (1990).

Jilka, et al. Increased osteoclast development after estrogen loss: mediation by interleukin–6. *Science* 257:88–91 (1992).

Kishimoto, et al. Interleukin–6 and its receptor: A paradigm for cytokines. *Science* 258:593–597. (1992).

Klein, et al. Interleukin–6 is the central tumor growth factor in vitro and in vivo in multiple myeloma. *Eur. Cytokine Net.* 1:193–201 (1990).

Levy, et al. Interleukin–6 antisense oligonucleotides inhibit the growth of human myeloma cell lines. *J. Clin. Invest.* 88:696–699. (1991).

Majumdar, et al. Stepwise mechanism of HIV reverse transcriptase: Primer function of phosphorothioate oligodeoxynucleotide. *Biochemistry*, 28:1340–1346. American Chemical Society (1989).

Miles, et al. AIDS Kaposi sarcoma–derived cells produce and respond to interleukin 6. *Proc. Natl. Acad. Sci.* 87:4068–4072. Medical Sciences, U.S.A. (1990).

Milligan, et al. Development of antisense therapeutics. Implications for cancer gene therapy. *Annals New York Academy of Sciences*, 716:228–241 (1994).

Nishimoto, et al. Oncostatin M, Leukemia inhibitory factor, and interleukin 6 induce the proliferation of human plasmacytoma cells via the common signal transducer, GP130. *J. Exp. Med.* 179:1343–1347. The Rockefeller University Press (1994).

Scala, et al. Expression of an exogenous interleukin 6 gene in human Epstein Barr virus B cells confers growth advantage and in vivo tumorigenicity. *J. Exp. Med.* 172:61–68. The Rockefeller University Press (1990).

Shuin, et al. The activity of topoisomerases is related to the grade and stage in human renal cell carcinoma. *AntiCancer Research*, 14:2621–2626. (1994).

Liu et al., "Interleukin–6 Signal Transducer gp130 Mediates Oncostatin M Signaling". *J. Biol. Chem.* 267(24): 16763–16766 (1992).

Stec, et al. Automated solid–phase synthesis, separation, and stereochemistry of phosphorothioate analogues of oligodeoxyribonucleotides. *J. Am. Chem. Soc.* 106:6077–6079 American Chemical Society (1984).

Stein, et al. Phosporthioate oligodeoxynucleotides antisense inhibitors of gene expression. *Pharmac. Ther.* 52:365–384. Pergamon Press Ltd., Great Britian (1992).

Takenawa, et al. Enhanced expression of interleukin–6 in primary human renal cell carcinomas. *Journal of the National Cancer Institute.* 83:1668–1672 (1991).

(List continued on next page.)

*Primary Examiner*—John L. LeGuyader
*Assistant Examiner*—Sean McGarry
*Attorney, Agent, or Firm*—Charles B. Cappellari; Carlos A. Fisher

[57] ABSTRACT

The present invention relates to oligonucleotides which are effective inhibitors of disease-associated cellular proliferation. In particular, it relates to the use of oligonulceotides which are substantially complementary to gp130 mRNA sequences. In the form of pharmaceutical compositions, these oligonucleotides are suitable for administration to human subjects for the treatment of abnormal cellular proliferation due to such diseases as cancer, autoimmune disorders and viral infection.

23 Claims, No Drawings

OTHER PUBLICATIONS

Vink, et al. Mouse plasmacytoma growth in vivo: enhancement by interleukin 6 (IL-6) and inhibition by antibodies directed against IL-6 or its receptor. *J. Exp. Med.* 172:997–1000. The Rockefeller University Press. (1990).

Uhlmann, et al., "*Antisense Oligonucleotides: A New Therapeutic Principle*", Chemical Reviews, 90(4):543–584, (Jun. 1990).

Gupta et al., "Silencing of gp130 Gene Expression by Antisense Ribozyme Technology Blocks CNTF Signal Transduction in Embryonal Carcinoma Cells", *Society for Neuroscience Abstracts*, 19:1–2 (1993).

Stull et al., "Antigene, Ribozyme and Aptamer Nucleic Acid Drugs: Progress and Prospects", Pharmaceutical Research 12(4):465–483 (1995).

Gura, T., "Antisense Has Growing Pains", Science 270:575–577 (1995).

OLIGONUCLEOTIDES SPECIFIC FOR CYTOKINE SIGNAL TRANSDUCER GP130 MRNA

This application is a continuation of application Ser. No. 08/476,634, filed Jun. 7, 1995 now U.S. Pat. No. 5,674,995.

FIELD OF THE INVENTION

The present invention relates to oligonucleotides which are effective inhibitors of cellular proliferation. In particular, it relates to oligonucleotides which are substantially complementary to gp130 mRNA sequences and their use as therapeutic agents.

BACKGROUND OF THE INVENTION

Cellular growth, function, differentiation and development are regulated by a variety of different mechanisms. Among the most important regulators of cells are the receptor-specific proteins called "cytokines". These proteins bind to specific membrane-associated receptors which, in turn, traduce intracellular signals that ulitmately regulate the expression of critical genes and thereby control many normal cellular functions such as the immune response and hematopoiesis. In addition, cytokine dysregulaton has been implicated in many different disease states, such as cancer, viral infection and autoimmune disorders.

Although individual cytokines differ in their specific biological activities, many redundancies exist. In particular, interleukin-6 ("IL-6") and the related cytokines oncostatin M ("OSM"), leukemia inhibiting factor ("LIF"), interleukin-11 ("IL-11"), and ciliary neurotrophic factor ("CNTF") exhibit many overlapping biological functions. These IL-6-like cytokines, or "IL-6 cytokines", function through a complex cell surface receptor system which involves the concerted action of a ligand-specific receptor and a common signal transducing molecule, gp130. (Kishimoto, et al., Science 258: 593–597 (1992); Hibi, et al., Cell 63: 1149–1157 (1990)). It is believed that the redundancy in the biological activity among IL-6 cytokines is attributable to their dependence on the common signal transducer, gp130. This redundancy is also demonstrated in the disease-associated cellular proliferation which is induced by the IL-6 cytokines. For example, IL-6, OSM and LIF have all been shown to induce the growth of myeloma cells (Nishimoto, et al., supra). In addition, IL-6 and OSM are both known to promote the growth of Kaposi's sarcoma (Miles et al., Proc. Nat. Acad. Sci. 87: 4068–4072 (1990)).

Recently, many investigators have focused on the suppression of IL-6 production as a potentially useful means of inhibiting the cytokine-induced cellular proliferation associated with various diseases. Vink, et al. (J. Exp. Med. 172: 997–1000(1990)) describe the inhibition of plasmacytoma growth in vivo by using antibodies directed against IL-6 or its receptor, IL-6R. Levy et al. (J Clin. Invest. 88: 696–699 (1991)) describe the use of antisense oligonucleotides which are complementary to the MRNA encoding the IL-6 protein. Fujita (PCT Application No. WO 94/25036) describes the use of antisense oligonucleotides which are complementary to the initiator codon of the mRNA encoding IL-6R.

However, because of the redundancy of biological activities among the IL-6 cytokines, the specific inhibition of IL-6 function may have little effect on the equivalent activities of the other members of this family of cytokines. It would therefore be desirable to inhibit the disease-associated activities of the entire family of IL-6 cytokines, and this is best accomplished by inhibiting their common signal transducer, gp130. In fact, monoclonal antibodies to gp130 inhibit the effects of all of the IL-6 cytokines (Nishimoto et al., J. Exp. Med. 179: 1343–1347 (1994)).

The field of "antisense therapeutics" refers to the use of oligonucleotides which are complementary to target nucleic acids, most usually mRNA, as regulators of nucleic acid function. An antisense oligonucleotide, i.e. an oligonucleotide having a nucleic acid sequence which is complementary to that of the "sense" nucleic acid to which it is targeted, can function in many different ways to modulate nucleic acid function. When the targeted nucleic acid is mRNA, it may function by preventing translation of the mRNA into protein or inhibiting the binding or translocation of ribosomes. When the targeted nucleic acid is DNA, it may prevent transcription into mRNA.

In addition to inhibiting the production and/or function of mRNA by a "sequence specific" antisense mechanism, the effect of certain oligonucleotides, and particularly phosphorothioate oligonucleotides, can be partially attributed to non-sequence specific mechanisms. Such mechanisms have been reported to account for some of the effects of phosphorothioate oligonucleotides as anti-viral agents. (Stein, et al., Pharmac. Ther. 52: 365–384 (1991); Majumdar, et al., Biochemistry 28: 1340 (1989)).

It is an object of the present invention to provide oligonucleotides which effectively inhibit disease-associated cellular proliferation. Such oligonucleotides are complementary to the mRNA encoding gp130, and function via sequence specific (antisense) and/or non-sequence specific mechanisms. A further objective of the present invention is to provide pharmaceutical compositions suitable for administration to human subjects comprising these oligonucleotides.

SUMMARY OF THE INVENTION

The present invention features oligonucleotides and methods for inhibiting disease-associated cellular proliferation. The preferred target site is the mRNA encoding the signal transducer, gp130. The preferred use of the oligonucleotides described herein is in the treatment of a patient suffering from cancer, such as renal cell carcinoma. Other uses of the present invention include detecting the presence of the gp130 mRNA by using the oligonucleotides as in vitro detection probes. These detection probes would be particularly useful in evaluating the effectiveness of other therapeutic agents in reducing gp130 mRNA levels.

The oligonucleotides of the present invention are based on the following preferred sequences:

| SEQ. ID. NO. 1 | GGCCCAGCGC GACTCCGCGG GCCTT |
|---|---|
| SEQ. ID. NO. 2 | CCTGTAGATT CAGTGGTGAG |
| SEQ. ID. NO. 3 | ACACAAACTG CAGTGAAATT AGAATG |
| SEQ. ID. NO. 4 | TACATGAAAA TAATCCATAC ATT |
| SEQ. ID. NO. 5 | GTTTATGATA GTATATTGCT CCTTA |
| SEQ. ID. NO. 6 | CCATAAACATT CTGTTCAAGC TGTC |
| SEQ. ID. NO. 7 | TGCCCATTCA GATTTTAAAG TGAAG |
| SEQ. ID. NO. 8 | GCTTTGCAAT CAGCAAACTT GTGTGT |
| SEQ. ID. NO. 9 | TACAGGATCA AAATTGATAT GATCTGATGT AACC |

-continued

| SEQ. ID. NO. 10 | GGCATCTTTG GTCCTATATT G |
| SEQ. ID. NO. 11 | AGGATCTGGA ACATTAGGC |
| SEQ. ID. NO. 12 | GCTCGAAGTG TTTTGTGAAG |

Oligonucleotides having nucleic acid sequences substantially corresponding to a preferred nucleic acid sequence and consisting essentially of the preferred nucleic acid sequence (i.e. having a nucleic acid sequence which is substantially the same) are also covered by the present invention.

Another aspect of the present invention is a method of inhibiting disease-associated proliferation of cells compromising the step of contacting the cells with a purified oligonucleotide 12 to 100 nucleotides in length, said oligonucleotide being substantially complementary to gp130 mRNA, wherein said oligonucleotide inhibits proliferation of cells in vivo or in vitro.

Other features and advantages of the invention are apparent from the following detailed description and the claims.

Detailed Description

The present invention concerns oligonucleotides which inhibit cellular proliferation. In order to more clearly describe the subject matter of the present invention, certain terms used herein shall be defined as follows unless otherwise indicated:

Antisense Oligonucleotide: "Antisense oligonucleotide" means an oligonucleotide which is complementary to a target "sense" nucleic acid, and functions at least partially by sequence-specific mechanisms to regulate the functioning of the target nucleic acid.

Complementary: "Complementary", when used to refer to a nucleic acid, means a nucleic acid of one polarity containing a sequence of nucleotides whose bases pair via Watson-Crick hydrogen bonds with the nucleotide bases of another nucleic acid of opposite polarity, i.e. adenine ("A") pairs with thymine ("T") or uracil ("U"), and guanine ("G") pairs with cytosine ("C"). For example, a nucleic acid having the sequence GCAU in the 5' to 3' direction is "complementary" to a nucleic acid having the sequence CGTA in the 3' to 5' direction. Use of the term complementary herein is intended to include those nucleic acids which are substantially complementary such that, despite occasional mismatches between the strands, a stable duplex will nevertheless be formed. The individual strands of a complementary nucleic acid pair can also be referred to as the plus ("(+)") or "sense" strand and the minus ("(-)") or "antisense" strand.

Disease-associated Cellular Proliferation: "Disease-associated cellular proliferation" means an abnormal level of cell division and/or growth which is caused by or associated with a particular disease such as cancer or viral infection.

Hybridize: "Hybridize" means the formation of a duplex between complementary nucleic acids via base pair interactions.

Liposome: "Liposome" means a vesicle composed of amphipathic lipids arranged in a spherical bilayer or bilayers.

Modified: "Modified", when used to refer to a nucleic acid, means a nucleic acid in which any of the natural structures have been altered. These include modifications to the phosphodiester linkages, the sugars (ribose in the case of RNA or deoxyribose in the case of DNA) and/or the purine or pyrimidine bases. Modified phosphodiester linkages include phosphorothioates, phosphotriesters, methylphosphonates and phosphorodithioates. "Modified dNTPs" refers to nucleoside triphosphates which, when incorporated into a nucleic acid, will result in the formation of modified nucleic acids.

Nucleic Acid Sequence: "Nucleic acid sequence", or "sequence", means both a nucleic acid having a particular sequence of nucleotides, and also the sequence or order of nucleotides present in a particular nucleic acid. Which of these two meanings applies will be apparent form the context in which this term is used.

Oligonucleotide: "Oligonucleotide" means an oligodeoxyribonucleotide having a defined nucleic acid sequence.

Pharmacologically compatible carrier: "Pharmacologically compatible carrier means a formulation to which the oligonucleotide can be added to facilitate its administration to a patient and/or efficacy without exhibiting any unacceptable levels of toxicity or pharmacologically adverse effects.

Phosphorothioate oligonucleotide: "Phosphorothioate oligonucleotide" means an oligonucleotide having all phosphorothioate linkages in place of naturally occurring phosphodiester linkages.

Phosphorothioate-containing oligonucleotide: "Phosphorothioate-containing oligonucleotide" means an oligonucleotide having at least one and as many as all phosphorothioate linkages. This term is intended to include phosphorothioate oligonucleotides.

Polarity: "Polarity" means the orientation of a nucleic acid polymer which is created when the C3 position of one deoxyribose (or ribose) moiety is linked together with the C5 of the adjacent deoxyribose (or ribose) moiety via a phosphate linkage. The polarity of nucleic acids is referred to as 5' to 3' or 3' to 5'.

Polymerase: "Polymerase" means an enzyme which is capable of catalyzing the sequential addition of nucleotides to a nucleic acid.

Primer: "Primer" means an oligonucleotide that is complementary to a template that hybridizes with the template to initiate synthesis by a polymerase, such as reverse transcriptase, and which is extended by the sequential addition of covalently bonded nucleotides linked to its 3' end that are complementary to the template.

Substantially Complementary: "substantially Complementary", when used to refer to a nucleic acid, means having a sequence such that not all of the nucleotides exhibit base pairing with the nucleotides of another nucleic acid, but the two nucleic acids are nonetheless capable of forming a stable hybrid under appropriate conditions.

Template: "Template" means the nucleic acid having the sequence of nucleotides which will provide the pattern and serve as substrate for producing a desired oligonucleotide. In order to serve as such, the template must also contain a sequence which is capable of hybridizing with a primer or, in the case of self-priming templates, capable of forming a self-priming region.

Therapeutically effective amount: "Therapeutically effective amount" means an amount which is effective in inhibiting disease-associated cellular proliferation and/or growth in a patient suffering from a disease associated with overproduction of IL-6. Preferably, the therapeutically effective amount relieves, to some extent one or more symptoms associated with the disease.

The development of therapeutic applications using oligonucleotides is now widespread. Although the precise mechanism of action of oligonucleotides as therapeutic agents is often difficult to determine, many proposed mechanisms have been suggested and any or all of these different mechanisms may act in concert to produce a desired result. One mechanism of action is based on antisense. Antisense oligonucleotides are generally designed to have sequences which are complementary to specific sequences found in target nucleic acids such as DNA, mRNA or precursor mRNA. By hybridizing to a specific sequence in the target nucleic acid, the antisense oligonucleotide interrupts the protein-encoding function of the DNA.

Some of the proposed mechanisms which may account for the antisense function of a particular oligonucleotide may include: cleavage of RNA in a RNA:DNA hybrid by an enzyme having RNase H activity; premature termination of mRNA transcription; prevention of translocation of the mRNA to the site for protein translation; interference with mRNA processing by hybridizing to an mRNA intron/exon; interference with mRNA function by hybridizing to non-protein coding (untranslated) regions; and/or interference with ribosome binding by hybridizing to an mRNA initiator codon. In summary, each of these sequence-specific antisense mechanisms act in some way to inhibit the expression of a particular gene.

In addition to sequence-specific antisense mechanisms, certain modified oligonucleotides can inhibit nucleic acid function via a non-sequence specific mechanism. In some instances, when the effects of antisense oligonucleotides are compared to "control" oligonucleotides which contain the same bases in randomized order, the control oligonucleotides also exhibit inhibition of protein production. Although the precise mechanism for such non-sequence specific mechanisms is not known, these effects have been attributed to the accidental inhibition of other essential genes by the control oligonucleotides. (See Milligan, et al., in *Antisense Therapeutics*; Development of Antisense Therapeutics, Annals of the New York Academy of Sciences, p. 228–247)

One potential explanation for non-sequence specific effects of oligonucleotides on proliferation of renal carcinoma cells is the inhibition of topoisomerase. Many anticancer agents with activity against renal cell carcinoma have been demonstrated to inhibit topoisomerase. (Shuin, et al., Anticancer Research 14: 2621–2626 (1994)). It is hypothesized that topoisomerase inhibition by phosphorothioate oligonucleotides may account for a portion of the observed antiproliferative effects attributable to the phosphorothioate oligonucleotide.

In any case, both sequence specific and non-sequence specific mechanisms may account for the effects of the oligonucleotides of the present invention. A complete understanding of the mechanisms of action is not necessary for the design of cellular function-inhibiting oligonucleotides.

The oligonucleotides of the present invention are complementary to the mRNA encoding gp130, and may inhibit gp130 production via antisense and/or other mechanisms. Therapeutic agents which inhibit the functioning of IL-6 and related cytokines, such as those which regulate the production of gp130, can be used to counteract the effects of overproduction of IL-6 cytokines.

The normal functioning of IL-6 involves the induction of IL-6 production by many different cell types, such as fibroblasts, macrophages, endothelial cells and keratinocytes, as a response to injury or infection. In the absence of injury or infection, these cells do not normally produce IL-6. IL-6 production results in an enhancement of the immune response via a variety of mechanisms which include B- and T- cell proliferation or differentiation as well as T-cell and macrophage activation.

However, IL-6 overproduction is implicated in many different disease states. For example, IL-6 hyperexpression in Epstein Barr virus infected B lymphocytes has been shown to be partially responsible for tumorigenicity (Scala et al., J. Exp. Med. 172: 61–68 (1990)). The overproduction of IL-6 by keratinocytes has been shown to play a causative role in the epidermal hyperplasia associated with psoriasis (Grossman et al., Proc. Nat. Acad. Sci. 86: 6367–6371 (1989)). Overproduction of IL-6 by renal carcinoma cells has been shown to be associated with increased metastases (Takenawa, et al., Journal of the National Cancer Institute 83(22): 1668–1672 (1991)). IL-6 also plays a reported role in the increase of bone resorption during menopause due to its enhancement of osteoclast development (Jilka et al., Science 257: 88–91 (1992); and Girasole et al., Journal of Clinical Investigation 89: 883–891 (1992)). Additionally, IL-6 has been shown to be a tumor growth factor for multiple myeloma cells (Klein, et al., Eur. Cytokine Net., 1(4): 193–201 (1990)). Other disease states which have been associated with IL-6 overproduction include plasma cell leukemia, cachexia, mesangial proliferative glomerulonephritis, Kaposi's sarcoma, rheumatoid arthritis, hypergammaglobulinemia, Castleman's disease, IgM gamopathy, cardiac myxoma and autoimmune insulin-dependent diabetes.

Thus, therapeutic agents which are designed to inhibit IL-6 function have a widespread therapeutic application. They can be used as a therapeutic agent in the treatment of any of the aforementioned disease states. The antisense oligonucleotides of the present invention are preferably used to treat renal cell carcinoma.

The oligonucleotides of the present invention can be either DNA or RNA, but are preferably DNA. The oligonucleotides can be prepared using any known chemical or enzymatic methods. Chemical synthesis can be conveniently performed according to the method described by Stec et al. (J. Am. Chem. Soc. 106: 6077–6079 (1984)) using the phosphoroamidite method and an automated synthesizer, such as Model 380-B (Applied Biosystems, Inc., Foster City, California).

The oligonucleotides included within the present invention can be either unmodified or modified. Modified oligonucleotides can be prepared by altering any of the natural structures of a nucleic acid. These structures include the phosphodiester linkages, the sugars (ribose in the case of RNA or deoxyribose in the case of DNA) and/or the purine or pyrimidine bases. Any modification can be made to an oligonucleotide as long as it does not render the oligonucleotide ineffective at hybridizing to the target nucleic acid or toxic, if to be used in vivo. This includes certain modifications which may diminish hybridization efficiency without completely preventing the formation of a stable duplex.

Preferred modifications are to the phosphodiester linkages to render them more stable in the presence of nucleases. Modifying the phosphodiester linkages may also enhance cellular uptake. Modified phosphodiester linkages include phosphorothioate, methylphosphonate, phosphorodithioate, or phosphoselenate linkages. The oligonucleotides may contain all modified linkages, a mixture of different modified linkages, a mixture of modified linkages and unmodified linkages, or any combination of these which are either selectively positioned, or present in different regions of the oligonucleotide as in a chimeric oligonucleotide. Oligonucleotides with modified internucleotide linkages can be synthesized in the same manner as unmodified oligonucleotides by known methods, including many of the methods discussed above.

Other examples of modifications include the incorporation of modified sugar groups such as alpha-anomers or the sugars incorporated into 2'-O-methyloligonucleotides. Also contemplated are modifications to the nucleotide purine or pyrimidine bases.

Preferably, the oligonucleotides of the present invention contain phosphorothioate linkages which increase stability, facilitate cellular uptake and may enable the oligonucleotides to inhibit cellular functions by sequence independent mechanisms as well as sequence specific antisense mechanisms.

The antisense oligonucleotides of the present invention are preferably 12 to 100 nucleotides in length. More preferably, these oligonucleotides are 14 to 50 nucleotides in length, and most preferably 18 to 35 nucleotides in length. Oligonucleotide length should be selected to optimize the efficiency of the oligonucleotide in inhibiting disease-associated cellular proliferation and/or growth. The existence of any modifications in the oligonucleotide will also influence the effects of length on overall efficiency of the oligonucleotide.

In order to determine the optimal oligonucleotide size, several factors should be taken into account. Oligonucleotides which are short have the advantage of being more easily internalized by cells. However, if they are not long enough, for example less than 10 bases, they may not form specific and stable hybrids with target sequence. On the other hand, longer oligonucleotides may hybridize to their targets with increased stability which may enhance translation arrest by preventing a ribosome from displacing the oligonucleotide. However, if the oligonucleotide is too long, for example greater than 150 bases, it may not be efficiently taken up by cells and/or could potentially be cytotoxic.

An oligonucleotide screening assay designed to mimic normal physiological conditions can be utilized to predict the efficiency with which the oligonucleotides hybridize in living cells. Such a screening assay is described by Nelson et al., in WO 95/03427

The oligonucleotides of the present invention are complementary to gp130 mRNA. The sequence of gp130 mRNA is reported by Hibi, et al., Cell 63: 1149–1157 (1990). Preferably, the target sequence is a protein coding region of the gp130 mRNA. The preferred oligonucleotides of the present invention are given by the following sequences:

| SEQ. ID. NO. 1 | GGCCCAGCGC GACTCCGCGG GCCTT |
| SEQ. ID. NO. 2 | CCTGTAGATT CAGTGGTGAG |
| SEQ. ID. NO. 3 | ACACAAACTG CAGTGAAATT AGAATG |
| SEQ. ID. NO. 4 | TACATGAAAA TAATCCATAC ATT |
| SEQ. ID. NO. 5 | GTTTATGATA GTATATTGCT CCTTA |
| SEQ. ID. NO. 6 | CCATAAACATT CTGTTCAAGC TGTC |
| SEQ. ID. NO. 7 | TGCCCATTCA GATTTTAAAG TGAAG |
| SEQ. ID. NO. 8 | GCTTTGCAAT CAGCAAACTT GTGTGT |
| SEQ. ID. NO. 9 | TACAGGATCA AAATTGATAT GATCTGATGT AACC |
| SEQ. ID. NO. 10 | GGCATCTTTG GTCCTATATT G |
| SEQ. ID. NO. 11 | AGGATCTGGA ACATTAGGC |
| SEQ. ID. NO. 12 | GCTCGAAGTG TTTTGTGAAG |

Two particularly preferred sequences are given by SEQ. ID. NO.s 3 and 5.

It is not necessary for the entire oligonucleotide sequence to be perfectly complementary to the target gp130 MRNA sequence. It is only necessary for the oligonucleotide to be "substantially complementary", i.e. capable of forming a stable hybrid with the target. Additional noncomplmentary nucleotides may be present in the antisense oligonucleotide at any location, for example at either the 3' or 5' terminus, or any other location therebetween. Such additional non-complementary nucleotides may serve to inhibit in-vivo degradation and/or enhance the effects of the oligonucleotide in interfering with gene expression. The amount of complementarity necessary to form a stable hybrid with the target sequence will depend on the types and amounts of modifications present, the types of bases involved in hydrogen bonding (e.g. G:C hydrogen bonding is stronger than A:T) and the length of the oligonucleotide.

In addition to their usefulness as therapeutic agents, the oligonucleotides described herein are also useful as diagnostic probes and as research tools, such as amplification primers. Utilizing labeled oligonucleotide probes which are specific for gp130 mRNA, the presence or amount of gp130 mRNA can be determined. The design and production of labeled oligonucleotide probes and their use in hybridization methods is easily accomplished by one of skill in the art.

Considerations for therapeutic use include oligonucleotide pharmacology and delivery. For use as therapeutic agents, the oligonucleotides must be pharmacologically suitable, i.e. they must exhibit minimal toxicity and suitable distribution and metabolism. Different pharmacological considerations can be evaluated using techniques which are known in the art.

Pharmaceutical compositions comprising the oligonucleotides in a pharmacologically acceptable carrier may be administered by a variety of different mechanisms which are well known to those of skill in the art. Such mechanisms include oral administration (inhalation or parenteral), injection (intravenous, intramuscular, subcutaneous, intraperitoneal), and topical administration (intranasally, cutaneous). Compositions which are suitable for each of these different mechanisms are routinely prepared and utilized.

Examples of pharmacologically acceptable carriers include aqueous solutions such as water, saline, buffers or carbohydrate solutions; and delivery vehicles such as liposomes, microspheres, or emulsions. Delivery vehicles can be utilized to enhance in vivo stability. Liposomes are preferred because of their ability to enhance intracellular delivery, their long circulation half-lifes, the ease of incorporation of receptor targeted molecules, their minimal toxicity and good biodegradability. Liposomes may be made by a variety of techniques known in the art. (See, for example, Bangham et al., J. Mol. Biol., 13: 238–252 (1965)). These methods generally involve first dissolving and mixing the lipids in an organic solvent, followed by evaporation. Then an appropriate amount of the aqueous phase is mixed with the lipid phase, and then allowed to incubate for a sufficient time for the liposomes to form. The aqueous phase will generally consist of the biomolecule in suspension with other solutes, such as buffers or sugars.

The exact dosage and number of doses of the pharmaceutical compositions described herein depends upon several factors such as the disease indication, the route of administration, the delivery vehicle and the oligonucleotide composition. Duration of treatment will depend on the effects of the treatment on the disease symptoms, and may include multiple daily doses for extended periods of time.

EXAMPLE I

Synthesis Of Oligonucleotides

Oligonucleotides containing phosphodiester linkages as well as modified linkages such as phosphorothioates can be synthesized by procedures well known in the art. For example, in Methods in Enzymology 154:287 (1987), Caruthers et al. describe a procedure for synthesizing oligonucleotides containing phosphodiester linkages by standard phosphoramidite solid-phase chemistry. Bhatt, U.S. Pat. No. 5,253,723, describes a procedure for synthesizing oligonucleotides containing phosphorothioate linkages. Klem et al., PCT WO92/07864 describe the synthesis of oligonucleotides having different linkages including methylphosphonate linkages.

EXAMPLE II

Inhibition Of Cellular Proliferation By Phosphorothioate Oligonucleotides

In order to test the effectiveness of several different phosphorothioate oligonucleotides complementary to mRNA for gp130 as inhibitors of cancer cell proliferation, two different cell lines were studied. Caki-1 cells (American Type Culture Collection, Rockville, Md.), a renal cell carcinoma derived cell line known to produce abnormally high levels of IL-6 were used, with 293 cells (American Type Culture Collection, Rockville, Md.), an EBV transformed normal renal cell line serving as the control.

Caki-1 or 293 cells were cultured in 48 well plates under conditions where the cells did not become confluent within the experimental time course. After the cells adhered to the plates (4–6 hours), cell culture medium containing the phosphorothioate oligonucleotides was added to the cultures, and medium alone was added to the no-oligonucleotide control cells. The cells were incubated under standard conditions (37° C., 50% $CO_2$), and on day 4 the medium was replaced. On day 7, the medium was removed and the cells released from the plates using trypsin. Cell numbers per well were determined by counting cell density using a hemocytometer. As shown in Table 2, 1 µM antisense oligonucleotides inhibited cell proliferation of Caki-1 cells by 70–90% but had little effect on the proliferation of control cells.

TABLE 2

INHIBITION OF CELLULAR PROLIFERATION BY PHOSPHOROTHIOATE OLIGONUCLEOTIDES

| Oligonucleotide | % Reduction of Caki-1 Cells |
| --- | --- |
| SEQ. ID. NO. 1 | 99 |
| SEQ. ID. NO. 2 | 64 |
| SEQ. ID. NO. 3 | 91 |
| SEQ. ID. NO. 4 | 66 |
| SEQ. ID. NO. 5 | 85 |
| SEQ. ID. NO. 6 | 62 |
| SEQ. ID. NO. 7 | 60 |
| SEQ. ID. NO. 8 | 71 |
| SEQ. ID. NO. 9 | 85 |
| SEQ. ID. NO. 10 | 62 |
| SEQ. ID. NO. 11 | 32 |
| SEQ. ID. NO. 12 | 43 |

EXAMPLE III

Inhibition Of Cellular Proliferation In Different Cell Lines

The oligonucleotides of the present invention would be expected to inhibit the proliferation of any cells that are representative of a disease state associated with IL-6 overproduction. To test this hypothesis, several cell lines were chosen which exhibit varying degrees of IL-6 overproduction: Caki-1 and Caki-2 (American Type Culture Collection, each renal cell carcinoma cell lines; 786-0, a primary renal cell adenocarcinoma (American Type Culture Collection CRL-1932); U266, a multiple myeloma (American Type Culture Collection TIB 196); and 293 cells, which served as the control.

Cells were seeded into flasks at a concentration of $1\times10_5$ cells per flask in the presence of medium which contained 1 µM of the oligonucleotide given by SEQ. ID. NO. 3. After 5 days, 1 ml of medium was collected from each flask. A 17 µl aliquout of each was electrophoresed on a 10% SDS-PAGE gel and then transferred to a nylon membrane. Levels of IL-6 were quantitated by immunoblot and visualized by the ECL western blotting analysis system (Amersham Life Sciences, Arlington Heights, Ill.). Signal was quantitated by use of an Ambis (San Diego, Calif.) image analyzer and corrected for final cell number. The IL-6 levels are expressed as a ratio of the level observed with Caki-1 cells.

Cell proliferation studies were performed as described in Example II.

As expected, the cell lines which exhibited the greatest amount of IL-6 production also exhibited the greatest decrease in cellular proliferation in the presence of the oligonucleotide. The results are given in Table 3.

TABLE 3

INHIBITION OF CELLULAR PROLIFERATION AND CORRELATION WITH IL-6 LEVELS

| Cell Line | % Reduction in Cellular Proliferation | Ratio of IL-6 Level |
| --- | --- | --- |
| Caki-1 | 88 | 1.00 |
| Caki-2 | 51 | 0.21 |
| 786-0 | 60 | 0.27 |
| U266 | 38 | 0.26 |
| 293 | 11 | 0.07 |

EXAMPLE IV

Effects Of Oligonucleotides On Cell-Surface Expression Of IL-6 Receptor

High affinity binding of IL-6 to a cell surface requires the presence of both IL-6R and gp130. Antisense oligonucleotides which are complementary to gp130 mRNA would therefore be expected to inhibit IL-6 binding. In order to assess the effects of the oligonucleotides of-the present invention on IL-6 binding, a flow cytometric analysis of Caki-1 cells was performed. Recombinant biotinlabeled IL-6 (R&D Systems, Inc., Minneapolis, MN) and Fluorescein isothiocyanate (FITC) labeled avidin were utilized to study IL-6 binding. To control for any nonspecific effects on cell surface protein expression, a monoclonal antibody to human HLA Class I molecules labeled with phycoerythrin (PE) was also utilized.

Caki-1 renal carcinoma cells were seeded in 24-well culture plates at densities that would allow four days of growth without reaching confluence. Cells were treated with 1 µM phosphorthioate oligonucleotides (final concentration) added directly to the cultures in sterile water. Cells were removed daily from the matrix by washing with phosphate buffered saline (PBS) containing 0.5 mM EDTA, washed by centrifugation in PBS, and resuspended in 25 µl of PBS at a concentration of $4 \times 10^6$/ml or less.

Cells were stained for cytometry by addition of 10 µl biotinylated IL-6 followed by a 60 minute incubation period at 4°. Following the initial incubation, 10 µl of FITC avidin solution and 5 µl of PE-anti-HLA was added. After an additional 30 minute incubation at 40° C., cells were washed twice in PBS and analyzed using flow cytometry. Scatter diagrams and mean fluorescence intensities (MFI) for both FITC and PE emission wavelengths were obtained. Percent-reductions in IL-6 or anti-HLA binding were calculated by subtracting the MFI values of the unstained cells from MFIs of stained, untreated controls and dividing this number into the difference in MFI between the unstained cells and the treated stained cells. Maximal effects were observed three days following exposure to the oligonucleotides. Results (averaged over four experiments) are summarized in Table 4 below:

TABLE 4

PERCENT REDUCTION OF IL-6R

| Oligonucleotide | Percent Reduction in of IL-GR | Percent Reduction of HLA |
|---|---|---|
| SEQ. ID. NO. 3 | 24 | 6 |
| SEQ. ID. NO 5 | 25 | 0 |

As shown, the antisense oligonucleotides inhibit IL-6 binding of the cells to IL-6R without concomitant reduction in the expression of the control cell surface protein.

EXAMPLE V

Effects Of Oligonucleotide On Expression of gp130 mRNA

One of the proposed mechanisms for the biological effects of antisense oligonucleotides involves the cleavage of target mRNA by the endonuclease RNAase H at the point of hybridization, followed by subsequent endonuclease digestion of the molecule. Such a phenomenon manifests itself experimentally as a reduction in the steady-state level of the specific mRNA, without concomitant reduction in nontargeted RNA molecules. In order to assess the effects of oligonucleotides on gp130 message levels, a Northern Blot analysis was performed on treated vs. untreated Caki-1 cells using $^{32}$P-labeled probes specific for both gp130, and the unrelated mRNA encoding Glyceraldehyde 3-phosphate dehydrogenase (GAPDH). One million cells were cultured at pre-confluent densities for 18 hours in the presence 400 nM of a phosphorothioate oligonucleotide SEQ. ID. NO. 3 encapsulated with cationic lipid (Lipfectin®, BRL Life Sciences, Gaithersburg, Md.) or with cationic lipid alone as a control. Following treatment, cells were harvested from the culture vessel and lysed for extraction of RNA using commercially available reagents and protocols (RNAzolB, CinnaBioTecx, Houston, Tex.). Polyadenylated RNA (MRNA) was then isolated using the Micro Fast Track system (Invitrogen Corp., San Diego, Calif.). Polyadenylated RNA was denatured with formaldehyde, and 3 µg was loaded into each of several lanes and electrophoresed through 1% agarose. The resolved RNA was transferred to a nitrocellulose membrane. The resultant "Northern blot" was exposed to both the gp130 and GAPDH labelled probes. Upon autoradiography of the blots, a clear reduction in the band intensity of gp130 but not GAPDH is observed in lanes containing RNA from treated cells relative to the lanes derived from untreated cells. Band intensity was quantified on an AMBIS phosphorimaging system (North Arlington, Ill.) which revealed a 40–50% reduction in the level of gp130 mRNA in the treated cells but no reduction in GAPDH message levels.

Although the invention is described in terms of specific embodiments, many modifications and variations of the present invention are possible in light of the teachings. It is, therefore, to be understood that within the scope of the appended claims the invention may be practiced otherwise than as specifically described.

---

We claim:

1. An oligonucleotide for inhibiting or reducing cytokine-induced cellular proliferation of cells, said oligonucleotide being up to 100 nucleotide bases in length and comprising a contiguous nucleotide base sequence selected from the group consisting of:

SEQ. ID. NO. 1    GGCCCAGCGC GACTCCGCGG GCCTT,
SEQ. ID. NO. 2    CCTGTAGATT CAGTGGTGAG,
SEQ. ID.    ACACAAACTG CAGTGAAATT AGAATG,

-continued

| | |
|---|---|
| SEQ. ID. NO. 3 | |
| SEQ. ID. NO. 4 | TACATGAAAA TAATCCATAC ATT. |
| SEQ. ID. NO. 5 | GTTTATGATA GTATATTGCT CCTTA. |
| SEQ. ID. NO. 6 | CCATAAACATT CTGTTCAAGC TGTC. |
| SEQ. ID. NO. 7 | TGCCCATTCA GATTTTAAAG TGAAG. |
| SEQ. ID. NO. 8 | GCTTTGCAAT CAGCAAACTT GTGTGT. |
| SEQ. ID. NO. 9 | TACAGGATCA AAATTGATAT GATCTGATGT AACC. |
| SEQ. ID. NO. 10 | GGCATCTTTG GTCCTATATT G. |
| SEQ. ID. NO. 11 | AGGATCTGGA ACATTAGGC. and |
| SEQ. ID. NO. 12 | GCTCGAAGTG TTTTGTGAAG. |

2. The oligonucleotide of claim 1, wherein said oligonucleotide contains one or more modified sugars, one or more modified internucleoside linkages, or one or more modified sugars and one or more modified internucleoside linkages.

3. The oligonucleotide of claim 2, wherein said modified internucleoside linkages are selected from the group consisting of phosphorothioate, methylphosphonate, phosphotriester, phosphorodithioate and phosphoselenate linkages.

4. The oligonucleotide of claim 3, wherein said modified internucleoside linkages are phosphorothioate linkages.

5. The oligonucleotide of claim 1, wherein said oligonucleotide is a phosphorothioate oligonucleotide.

6. The oligonucleotide of claim 1, wherein said oligonucleotide is up to 50 nucleotides in length.

7. The oligonucleotide of claim 1, wherein said oligonucleotide is up to 35 nucleotides in length.

8. The oligonucleotide of claim 1, wherein said nucleotide base sequence consists of:

SEQ. ID. NO. 1 GGCCCAGCGC GACTCCGCGG GCCTT.

9. The oligonucleotide of claim 1, wherein said nucleotide base sequence consists of:

SEQ. ID. NO. 2 CCTGTAGATT CAGTGGTGAG.

10. The oligonucleotide of claim 1, wherein said nucleotide base sequence consists of:

SEQ. ID. NO. 3 ACACAAACTG CAGTGAAATT AGAATG.

11. The oligonucleotide of claim 1, wherein said nucleotide base sequence consists of:

SEQ. ID. NO. 4 TACATGAAAA TAATCCATAC ATT.

12. The oligonucleotide of claim 1, wherein said nucleotide base sequence consists of:

SEQ. ID. NO. 5 GTTTATGATA GTATATTGCT CCTTA.

13. The oligonucleotide of claim 1, wherein said nucleotide base sequence consists of:

SEQ. ID. NO. 6 CCATAAACATT CTGTTCAAGC TGTC.

14. The oligonucleotide of claim 1, wherein said nucleotide base sequence consists of:

SEQ. ID. NO. 7 TGCCCATTCA GATTTTAAAG TGAAG.

15. The oligonucleotide of claim 1, wherein said nucleotide base sequence consists of:

SEQ. ID. NO. 8 GCTTTGCAAT CAGCAAACTT GTGTGT.

16. The oligonucleotide of claim 1, wherein said nucleotide base sequence consists of:

SEQ. ID. NO. 9 TACAGGATCA AAATTGATAT GATCTGATGT AACC.

17. The oligonucleotide of claim 1, wherein said nucleotide base sequence consists of:

SEQ. ID. NO. 10 GGCATCTTTG GTCCTATATT G.

18. The oligonucleotide of claim 1, wherein said nucleotide base sequence consists of:

SEQ. ID. NO. 11 AGGATCTGGA ACATTAGGC.

19. The oligonucleotide of claim 1, wherein said nucleotide base sequence consists of:

SEQ. ID. NO. 12 GCTCGAAGTG TTTTGTGAAG.

20. The oligonucleotide of any one of claims 8–19, wherein said oligonucleotide contains one or more modified sugars, one or more modified internucleoside linkages, or one or more modified sugars and one or more modified internucleoside linkages.

21. The oligonucleotide of claim 20, wherein said modified internucleoside linkages are selected from the group consisting of phosphorothioate, methylphosphonate, phosphotriester, phosphorodithioate and phosphoselenate linkages.

22. The oligonucleotide of claim 21, wherein said modified internucleoside linkages are phosphorothioate linkages.

23. The oligonucleotide of any one of claims 8–19, wherein said oligonucleotide is a phosphorothioate oligonucleotide.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
　　　　( A ) LENGTH: 25 base pairs
　　　　( B ) TYPE: nucleic acid (C) STRANDEDNESS: single
(D) TOPOLOGY: linear (xi) SEQUENCE DESCRIPTION: SEQ ID NO:1:

GGCCCAGCGC GACTCCGCGG GCCTT 25

(2) INFORMATION FOR SEQ ID NO:2:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:2:

CCTGTAGATT CAGTGGTGAG 20

(2) INFORMATION FOR SEQ ID NO:3:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:3:

ACACAAACTG CAGTGAAATT AGAATG 26

(2) INFORMATION FOR SEQ ID NO:4:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:4:

TACATGAAAA TAATCCATAC ATT 23

(2) INFORMATION FOR SEQ ID NO:5:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:5:

GTTTATGATA GTATATTGCT CCTTA 25

(2) INFORMATION FOR SEQ ID NO:6:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:6:

CCATAAACAT TCTGTTCAAG CTGTC 25

(2) INFORMATION FOR SEQ ID NO:7:

(i) SEQUENCE CHARACTERISTICS:
(A) LENGTH: 25 base pairs
(B) TYPE: nucleic acid
(C) STRANDEDNESS: single
(D) TOPOLOGY: linear (x i) SEQUENCE DESCRIPTION: SEQ ID NO:7:

TGCCCATTCA GATTTTAAAG TGAAG    25

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (x i) SEQUENCE DESCRIPTION: SEQ ID NO:8:

GCTTTGCAAT CAGCAAACTT GTGTGT    26

(2) INFORMATION FOR SEQ ID NO:9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (x i) SEQUENCE DESCRIPTION: SEQ ID NO:9:

TACAGGATCA AAATTGATAT GATCTGATGT AACC    34

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (x i) SEQUENCE DESCRIPTION: SEQ ID NO:10:

GGCATCTTTG GTCCTATATT G    21

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (x i) SEQUENCE DESCRIPTION: SEQ ID NO:11:

AGGATCTGGA ACATTAGGC    19

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (x i) SEQUENCE DESCRIPTION: SEQ ID NO:12:

GCTCGAAGTG TTTTGTGAAG    20